(12) United States Patent
Jakobsen et al.

(10) Patent No.: US 11,400,225 B2
(45) Date of Patent: Aug. 2, 2022

(54) PISTON ROD BRAKE MECHANISM

(71) Applicant: Novo Nordisk A/S, Bagsvaerd (DK)

(72) Inventors: Nikolaj Eusebius Jakobsen, Soeborg (DK); Steffen Hansen, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 373 days.

(21) Appl. No.: 16/612,572

(22) PCT Filed: May 7, 2018

(86) PCT No.: PCT/EP2018/061699
§ 371 (c)(1),
(2) Date: Nov. 11, 2019

(87) PCT Pub. No.: WO2018/206494
PCT Pub. Date: Nov. 15, 2018

(65) Prior Publication Data
US 2020/0206428 A1    Jul. 2, 2020

(30) Foreign Application Priority Data

May 11, 2017  (EP) ..................................... 17170660

(51) Int. Cl.
*A61M 5/315*  (2006.01)
*A61M 5/20*   (2006.01)
*A61M 5/24*   (2006.01)

(52) U.S. Cl.
CPC .......... *A61M 5/31501* (2013.01); *A61M 5/20* (2013.01); *A61M 5/24* (2013.01); *A61M 5/31553* (2013.01); *A61M 5/31568* (2013.01); *A61M 2005/2444* (2013.01); *A61M 2205/0294* (2013.01); *A61M 2205/50* (2013.01); *A61M 2205/502* (2013.01); *A61M 2205/581* (2013.01); *A61M 2205/582* (2013.01)

(58) Field of Classification Search
CPC ...... A61M 5/31501; A61M 5/20; A61M 5/24; A61M 5/31553; A61M 5/31568; A61M 2005/2444; A61M 2205/0294; A61M 2205/50; A61M 2205/502; A61M 2205/581; A61M 2205/582
See application file for complete search history.

(56) References Cited

U.S. PATENT DOCUMENTS

| 7,967,795 B1 | 6/2011 | Cabiri |
| 8,608,708 B2 | 12/2013 | Cowe |
| 10,252,005 B2 | 4/2019 | Row et al. |
| 10,279,118 B2 | 5/2019 | Oakley et al. |
| 2009/0093792 A1 | 4/2009 | Gross et al. |
| 2010/0114025 A1 | 5/2010 | Moller |
| 2013/0211330 A1 | 8/2013 | Pedersen et al. |
| 2015/0265776 A1 | 9/2015 | Beek et al. |
| 2016/0213853 A1* | 7/2016 | Despa ............... A61M 5/31548 |

FOREIGN PATENT DOCUMENTS

| CN | 102596291 B | 11/2014 |
| CN | 105377331 A | 3/2016 |
| CN | 105722539 A | 6/2016 |

(Continued)

*Primary Examiner* — Dung T Ulsh
(74) *Attorney, Agent, or Firm* — Wesley Nicolas (57) ABSTRACT

The invention provides a pen-type injection device (1) with a piston rod brake mechanism for improving the determination of an expelled dose.

10 Claims, 5 Drawing Sheets

(56) References Cited

FOREIGN PATENT DOCUMENTS

| | | | |
|---|---|---|---|
| GB | 787963 | A | 12/1957 |
| JP | 2009183772 | A | 8/2009 |
| JP | 2013534164 | A | 9/2013 |
| WO | 2006/128794 | | 12/2006 |
| WO | 2009049858 | A1 | 4/2009 |
| WO | 2011023629 | A1 | 3/2011 |
| WO | 2011023738 | A1 | 3/2011 |
| WO | 2015055642 | A1 | 4/2015 |
| WO | 2015071354 | A1 | 5/2015 |
| WO | 2016001292 | A1 | 1/2016 |
| WO | 2016001293 | A1 | 1/2016 |
| WO | 2016038445 | A1 | 3/2016 |

\* cited by examiner

Fig. 13

PISTON ROD BRAKE MECHANISM

CROSS-REFERENCE TO RELATED APPLICATIONS

This application is a 35 U.S.C. § 371 National Stage application of International Application PCT/EP2018/061699 (published as WO 2018/206494), filed May 7, 2018, which claims priority to European Patent Application 17170660.9, filed May 11, 2017, the contents of all above-named applications are incorporated herein by reference.

FIELD OF THE INVENTION

The present invention relates to injection devices capable of expelling one or more doses of drug from a drug reservoir.

BACKGROUND OF THE INVENTION

In the diabetes care segment parenteral drug administration carried out using a traditional vial and syringe system is increasingly being substituted by administration using a pen injection device. Pen injection devices are particularly convenient in that they allow the user to perform a dosed injection from a prefilled drug reservoir without first having to manually transfer the particular dose from one reservoir (the vial) to another (the syringe).

Predominantly, two types of pen injection devices are available, durable injection devices being capable of delivering one or more doses of drug from a prefilled drug cartridge which can be loaded into the device before use and replaced after exhaustion, and disposable injection devices being capable of delivering one or more doses of drug from a prefilled and non-exchangeable drug cartridge. Each of these types of pen injection devices are, or may in principle be, realised in various sub-types, such as e.g. single shot devices adapted to deliver only one dose from a drug cartridge, multi-shot devices capable of delivering a plurality of doses from a drug cartridge, manual devices, where the user provides the force needed for injection, automatic devices having a built-in energy source releasable to occasion the injection, fixed dose devices adapted to deliver a predetermined dose of drug, variable dose devices offering delivery of different doses of drug, settable by the user, etc.

As the labels suggest a durable injection device is intended for use over a considerable period of time during which multiple drug cartridges are exhausted and replaced, whereas a disposable injection device is intended for use until its dedicated drug cartridge is exhausted, after which the entire injection device is discarded.

In the treatment of diabetes it is advisable to keep a log of the administered doses of a particular drug (e.g. insulin or glp-1), as well as the respective times of dose administration. Some injection devices accordingly offer electronic dose capturing and the opportunity to review dose related information on a digital display.

Automatic injection devices are often powered by either a compression spring or a torsion spring, although alternatives to a spring may be used.

The FlexTouch® insulin injection device, manufactured by Novo Nordisk A/S, is an example of an automatic pen-type injection device, where the drug expelling mechanism is powered by a torsion spring. The torsion spring is tensioned during dose setting and released by slight depression of an injection button. When released the torsion spring causes rotation of a drive tube which in return causes rotation of a piston rod. The rotation of the piston rod is converted to a helical displacement thereof relative to an exterior housing. A piston rod foot is coupled rotationally freely to the distal end of the piston rod and serves to transfer a force from the piston rod to a rubber piston in an insulin containing cartridge, which rubber piston is accordingly translated to effect a dose delivery.

The drug expelling mechanism provides audible feedback in the form of a click sound for each expelled unit of insulin, correlated with a specific angular displacement of a component of the drug expelling mechanism, and the actually expelled dose may thus be determined by registering the number of emitted clicks. However, in the initial phase of an insulin expelling action the spring driven components move very fast due to axial compression of resilient parts of the injection device, particularly the piston. This means that the clicks produced during the first 3-5 expelled units can be difficult to distinguish. In fact, even a precise electronic detection may be challenging. While this issue may be more dominant within automatic injection devices it is indeed also relevant to manual injection devices, where it can be difficult for the user to control the speed of depression of the injection button in the initial phase of a dose expelling action.

SUMMARY OF THE INVENTION

It is an object of the invention to eliminate or reduce at least one drawback of the prior art, or to provide a useful alternative to prior art solutions.

In particular, it is an object of the invention to provide an injection device for which an output produced in an initial phase of a dose expelling action is easier to detect, enabling a more accurate determination of the expelled dose.

It is a further object of the invention to provide an injection device where a repeated output is produced more uniformly throughout a dose expelling action.

In the disclosure of the present invention, aspects and embodiments will be described which will address one or more of the above objects and/or which will address objects apparent from the following text.

An injection device embodying the principles of the invention comprises a dose expelling mechanism operable to expel a liquid substance, such as a drug, from a reservoir carrying a piston by helical movement of a piston actuator, means for producing a detectable output in response to a predetermined angular displacement of the piston actuator, and a contact surface rotationally locked with respect to the piston actuator and arranged in, or adapted to be arranged in, contact with a non-rotating part. The contact surface and the non-rotating part thereby undergo relative rotational motion during angular displacement of the piston actuator. This relative rotational motion occurs under the influence of friction in the contact interface between said contact surface and said non-rotating part, the friction braking the initial rotation of the piston actuator, whereby more easily distinguishable outputs are produced in the initial phase of a dose expelling action performed on or by the injection device. The contact between the contact surface being rotationally locked with respect to the piston actuator and the non-rotating part may be a sealing contact in the sense that at least over a portion of the contact interface fluid is unable to pass.

In a first aspect of the invention an injection device according to claim 1 is provided. Thereby, a pen-type injection device is provided, which injection device comprises a housing extending along a general axis, a cartridge comprising a cartridge body, a penetrable septum, and a piston, together defining a variable volume reservoir adapted to hold a liquid substance, and a dose expelling mechanism for administering a dose of the liquid substance from the cartridge. The cartridge is rotationally fixed with respect to the housing. The penetrable septum may be self-sealing, i.e. capable of re-establishing a sealing effect after penetration and withdrawal of a portion of an injection needle. The piston may be made of rubber or may at least comprise a peripheral rubber layer.

The dose expelling mechanism encompasses a piston rod structure comprising a piston rod threadedly engaged with the housing, e.g. with a nut member in or of the housing, and configured to rotate about the general axis, and thereby undergo helical displacement relative to the housing, during dose expelling, the helical displacement being correlated with an amount of drug administered. The dose expelling mechanism also encompasses a piston rod foot rotationally locked to the piston rod and adapted to interface with, e.g. abut, the piston. The piston rod foot may be an integral portion of the piston rod or a separate part attached to the piston rod.

The injection device further comprises output means for producing a detectable output in response to the piston rod structure undergoing a specific angular displacement relative to the housing. This specific angular displacement corresponds to a specific amount of drug being expelled from the cartridge. For example, if the injection device is configured to expel a dose of drug which can be set in certain increments each produced detectable output may correspond to expelling of one such increment. The output means may be adapted to produce the detectable output based on determined angular displacements of the piston rod structure itself or of a component rotationally locked with respect to the piston rod structure.

Importantly, the injection device also comprises a brake mechanism affecting rotational motion of the piston rod. The brake mechanism comprises a first contact surface forming part of the cartridge body, and a second contact surface which is rotationally locked with respect to the piston rod structure and which, at least during use of the injection device, is arranged in mechanical contact with the first contact surface. Thereby, the first contact surface and the second contact surface undergo relative rotational motion during dose expelling under the influence of a braking frictional force.

For example, the second contact surface may form part of the piston, and the piston and the piston rod structure may be rotationally interlocked, i.e. no relative angular displacement (with respect to the general axis) between the piston and the piston rod structure can occur.

Such a rotational coupling between the piston and the piston rod structure results in a greater resistance to rotational movement of the piston rod structure in the initial phase of the dose expelling action than in the prior art where the piston is compressed linearly. The predominant reason for this is that an axial compression of the piston, as seen in the prior art, involves little or no movement between the piston periphery and the interior surface of the cartridge body, whereas when the piston and the piston rod structure are rotationally interlocked the piston periphery is forced to move relative to the cartridge body when the piston rod structure rotates, thereby introducing an additional resistance in the form of a viscous friction force. This friction force is velocity dependent, i.e. it is more pronounced at attempts to move the piston fast.

The initial rotation of the piston rod structure is thus retarded, increasing the time it takes to undergo the specific angular displacement, and the first 3-5 detectable outputs are resultantly produced over a greater time period which allows for easy distinction of two successive outputs. This may be particularly advantageous when small doses are expelled. Furthermore, the initial retarding of the piston rod structure provides more uniformly distributed outputs over the entire dose expelling action, which may prevent situations where users worry if unevenly distributed outputs reflect a malfunction of the injection device.

The detectable output may be a tactile output, an audible output, or both a tactile and an audible output. This allows a user to feel and/or hear the output, and since each output is correlated with a specific amount of drug being expelled a total amount expelled in the course of one dose expelling action may be determined by the user counting the number of times (s)he feels and/or hears the output. The retarding of the initial rotation of the piston rod structure allows the user to clearly distinguish each produced output, whether it is a tactile output such as e.g. a vibration or an audible output such as e.g. an abrupt sound.

As an alternative to a tactile and an audible output, for example an optical output or a magnetic output may be produced.

The injection device may further comprise a detection mechanism configured to electronically register the detectable output, thereby offering automatic dose capturing and freeing the user from performing manual counting. Such a detection mechanism may be implemented in various configurations. For example, if the piston rod structure, or a component rotationally locked with respect to the piston rod structure, comprises a magnet then a stationary sensor may be provided for measuring a change in the magnetic field produced during rotation of the piston rod structure, and a processor may be provided for processing the sensor measurements.

In exemplary embodiments of the invention the output means comprises a deflectable housing portion capable of deflection relative to other housing portions and an activation element rotationally locked with respect to the piston rod structure, said activation element being arranged to cause a deflection of the deflectable housing portion in response to undergoing the specific angular displacement relative to the housing together with the piston rod structure, and the detection mechanism comprises a sensor arranged on the deflectable housing portion, which sensor is adapted to detect a deflection of the deflectable housing portion, and a processor electronically connected with the sensor and configured to process deflections detected by the sensor.

The piston rod foot may comprise a plurality of, e.g. circumferentially equidistantly, spaced protrusions which are pressed into an end portion of the piston. Thereby, a symmetric torque distribution may be transferred from the piston rod structure to the piston in order to slave the piston during rotation of the piston rod structure. In particular embodiments of the invention the piston rod foot comprises two diametrically opposite such protrusions.

Alternatively, the piston may comprise a first interface material having a first hardness and a first compression set, and the piston rod foot may comprise a second interface material arranged in pressurised abutment with the first interface material and having a second hardness which is smaller than the first hardness and a second compression set which is higher than the first compression set. Thereby a sticking connection between the piston and the piston rod foot may be provided to ensure joint rotation of the piston and the piston rod structure.

As an alternative to forming part of the piston, the second contact surface may form part of the piston rod foot, whereby a retarding of the initial rotation of the piston rod structure may be achieved without a rotationally interlocked connection to the piston. For example, the piston rod foot may be provided with a lip-like structure, e.g. of rubber, arranged, or adapted to be arranged, in contact with an interior surface of the cartridge body.

In particular embodiments of the invention the second contact surface is formed from the second interface material mentioned above and the desired retarding of the initial piston rod structure movement is thus achieved by a combination of a rotating piston and a rotating piston rod foot having respective surfaces sliding along the interior surface of the cartridge body.

The injection device may further comprise a power unit adapted to release energy to cause the piston rod structure to rotate. The power unit may be or comprise a spring member, such as e.g. a compression spring or a torsion spring, a compressed gas actuator, an electrochemical actuator, a wax actuator, a shape memory alloy, or a like structure being capable of storing and releasing energy.

In a second aspect of the invention a pen-type injection device is provided comprising a) a housing extending along a general axis, b) a cartridge comprising a cartridge body, a penetrable septum, and a piston, together defining a variable volume reservoir adapted to hold a liquid substance, the cartridge being rotationally fixed with respect to the housing, c) a dose expelling mechanism for expelling a dose of the liquid substance from the cartridge, comprising a piston rod structure for advancing the piston, the piston rod structure comprising a piston rod threadedly engaged with the housing and adapted to rotate and thereby undergo helical motion relative to the cartridge body during dose expelling, d) output means producing a detectable output at an angular displacement of the piston rod which corresponds to expelling of a predetermined dose increment, a total number of detectable outputs produced during a dose expelling event thereby being indicative of a size of an expelled dose, and e) detection means adapted to electronically register the detectable output. The pen-type injection device further comprises a brake mechanism configured to retard rotational motion of the piston rod, the brake mechanism comprising a first contact surface forming part of the piston, and a second contact surface arranged, or adapted to be arranged, in contact with the first contact surface, the second contact surface being rotationally locked with respect to the piston rod.

An injection device is thereby provided, wherein friction in the contact interface between the piston and the second contact surface brakes the rotational motion of the piston rod, resulting in more distinguishable outputs being produced by the output means in the initial phase of a dose expelling action performed on or by the injection device The piston rod structure may further comprise a piston rod foot adapted to interface with the piston. The piston rod foot may be rotationally locked to the piston rod, or it may be rotationally independent of the piston rod. In cases where the piston rod foot is rotationally locked to the piston rod the second contact surface may form part of the piston rod foot, and the first contact surface may constitute a portion of a proximal end of the piston. In exemplary embodiments the piston rod foot forms part of the piston rod.

In other cases, e.g. where the piston rod foot is rotationally independent of the piston rod, the second contact surface may form part of the piston rod, such as e.g. of a distal end portion of the piston rod, and the first contact surface may constitute a portion of a proximal end of the piston, e.g. a recess formed to tightly receive the distal end portion of the piston rod.

The output means and the detection means may e.g. be realised as exemplified in the above.

As used herein, the terms "distal" and "proximal" denote positions at or directions along a drug delivery device, where "distal" refers to the drug outlet end and "proximal" refers to the end opposite the drug outlet end.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein.

DESCRIPTION OF EXEMPLARY EMBODIMENTS

In the figures like structures are mainly identified by like reference numerals.

When in the following relative expressions, such as "clockwise" and "counter-clockwise", "left" and "right", etc. are used, these refer to the appended figures and not necessarily to an actual situation of use. The shown figures are schematic representations for which reason the configuration of the different structures as well as their relative dimensions are intended to serve illustrative purposes only.

Figure 1:
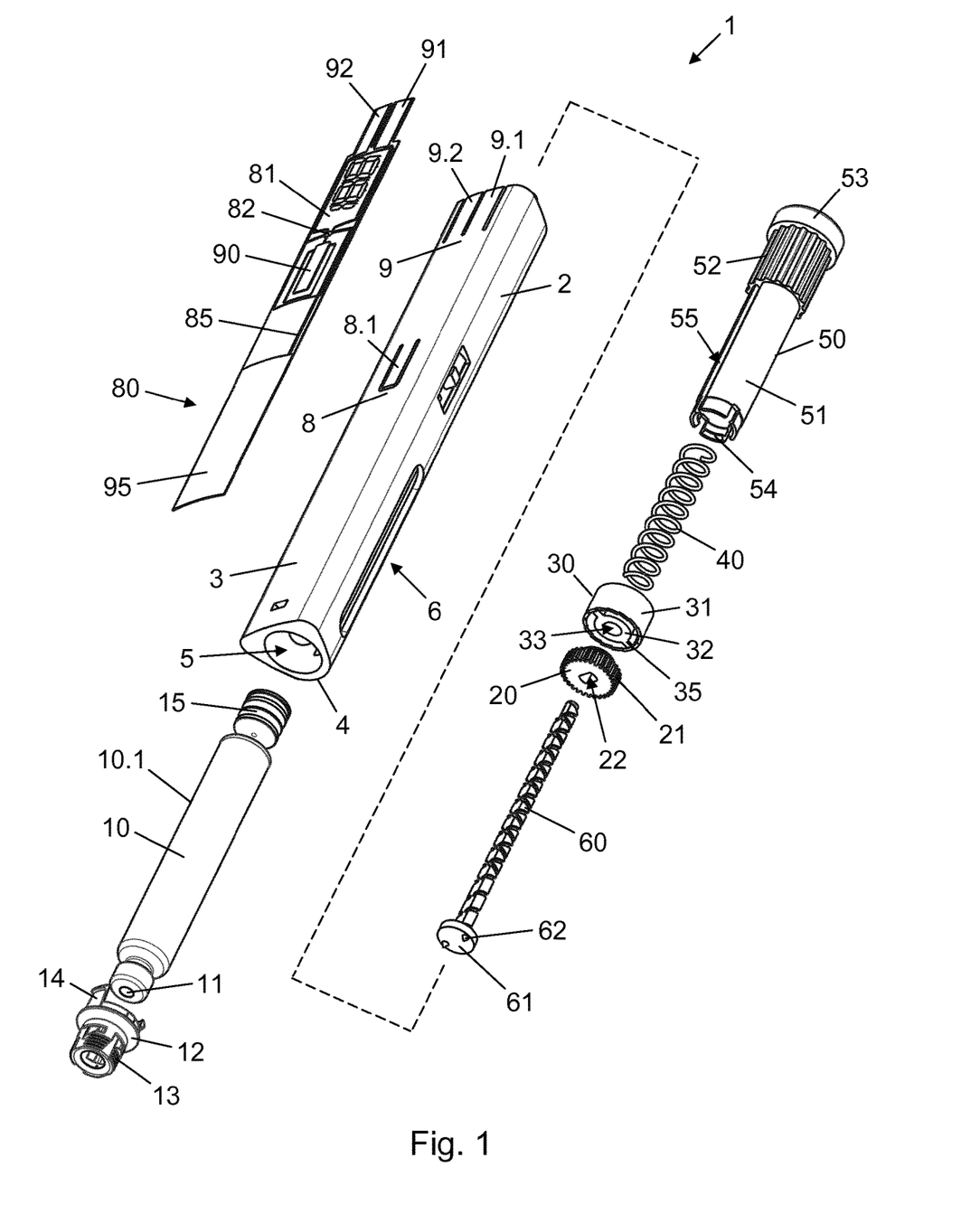
FIG. 1 is an exploded view of an injection device according to an exemplary embodiment of the invention.

FIG. 1 is an exploded view of a pen injection device 1 according to an exemplary first embodiment of the invention. The pen injection device 1 comprises a cylindrical housing 2 having a slightly curved information display surface 3 and a more conventionally curved opposing surface 4. The housing 2 accommodates a drug containing cartridge 10, which has been inserted through an opening 5 at a distal end thereof. The cartridge 10, which has a cartridge body 10.1 of mostly cylindrical shape, is closed at its distal end by a penetrable self-sealing septum 11 and at its proximal end by a rubber piston 15, is held within the housing 2 by a cartridge holder 12, being snapped to a proximal interior surface of the housing 2 by a pair of snap arms 14. The cartridge holder 12 further has a needle mount 13 and thereby serves as an attachment interface for an injection needle unit (not shown).

The housing 2 is provided with a longitudinal window 6 for inspection of the cartridge contents and further accommodates both a dose setting mechanism and an injection mechanism. The piston 15 in the cartridge 10 is adapted to be displaced by an elongated dual-threaded piston rod 60 of non-circular cross-section arranged to advance helically through a nut member 17 (see FIG. 3a) forming part of the housing 2. The distal end of the piston rod 60 is radially enlarged, providing a piston rod foot 61 adapted to mechanically interact with the piston 15. Two opposing spikes 62 extend axially in the distal direction from a distal end face of the piston rod foot 61. When the distal end face of the piston rod foot 61 abuts a proximal end face of the piston 15, the exterior of which comprises a rubber material, the spikes 62 have penetrated into the rubber to reside therein, establishing a rotational interlocking connection between the piston rod 60 and the piston 15. During drug expelling the piston rod 60 exerts a pressure on and applies a torque to the piston 15 via the piston rod foot 61 as a result of being actuated by a setting nut 30, as will be described further below.

The setting nut 30 has an outer annular wall 31 and an inner nut structure 32 with a circular opening 33 for receiving the piston rod 60. The inner nut structure 32 is radially separated from the outer annular wall 31 by an opposing pair of spacer legs 35. A clutch 20 is arranged distally of the setting nut 30 and has a toothed rim 21 and a central opening 22 of noncircular configuration for mating engagement with the piston rod 60, providing a rotational interlocking of the two. The clutch 20 is axially movable within the housing 2 between a proximal dose setting position, in which it is rotationally locked to the housing 2, and a distal dose expelling position, in which it is free to rotate with respect to the housing 2.

A dose dial knob 50 extends into the housing 2 from a proximal end thereof. The dose dial knob 50 comprises a cylindrical main body 51 which is rotatable about a longitudinal axis of the housing 2 by manipulation of an end button 53. A corrugated collar 52 is provided at the main body 51 just distally of the end button 53. The end button 53 has a larger diameter than the main body 51 which serves to limit distal movement of the dose dial knob 50 relative to the housing 2. A number of hooked fingers 54 are provided at the distal end of the main body 51 for engagement with a hooked stub 23 (see FIG. 3a) on the clutch 20, providing an axially interlocking connection between the dose dial knob 50 and the clutch 20. A pair of opposing slots 55 extends longitudinally from the corrugated collar 52 to the hooked fingers 54. Each slot 55 is adapted to receive one of the spacer legs 35, providing a rotationally interlocked, but axially free, connection between the dose dial knob 50 and the setting nut 30.

A compression spring 40 is arranged to act between an interior surface of the end button 53 and a proximal surface of the setting nut 30.

With respect to the housing 2 in a central area 8 of the information display surface 3 some wall material has been removed to provide a radially deflectable central cantilever arm 8.1 and in a proximal area 9 of the information display surface 3 more wall material has been removed to provide a forward indicating radially deflectable proximal cantilever arm 9.1 and a backward indicating radially deflectable proximal cantilever arm 9.2.

A flexible label 80 is adhered to the information display surface 3. The label 80 carries printed electronics in the form of a display 81, a chip 82 comprising a processor and a memory module, a central piezo sensor 90, a first proximal piezo sensor 91, a second proximal piezo sensor 92, a battery 95, and various leads 85 electrically connecting the chip 82 with each of the other electronic components. The label 80 is mounted on the information display surface 3 such that the central piezo sensor 90 is positioned on the central cantilever arm 8.1, the first proximal piezo sensor 91 is positioned on the forward indicating radially deflectable proximal cantilever arm 9.1, and the second proximal piezo sensor 92 is positioned on the backward indicating radially deflectable proximal cantilever arm 9.2.

Figure 2:
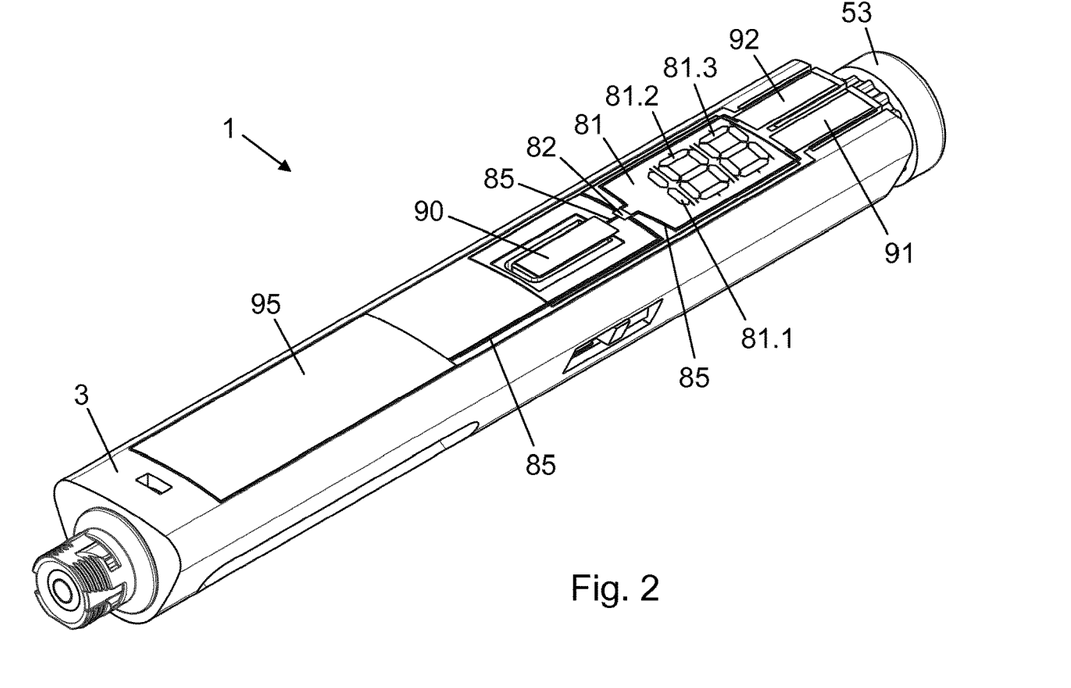
FIG. 2 is a perspective view of the injection device of FIG. 1, FIGS. 3a and 3b are longitudinal section views of a portion of the injection device showing, respectively, the injection device in a state just before setting of the first dose to be delivered and in a state just after delivery of the first dose, before release of the injection button.

FIG. 2 shows the pen injection device 1 in an assembled state detailing the label 80 adhered to the information display surface 3. The display 81 is a 16-segment electrochromic display comprising a 2-segment hundreds digit 81.1 and two 7-segment tens, respectively units digits 81.2, 81.3. The display 81 is capable of showing dose numbers in the range [0 units; 199 units], controlled by the chip 82. The central piezo sensor 90 is bent during a radial deflection of the central cantilever arm 8.1 and will resultantly emit a short peak signal which is detected by the chip 82. Similarly, the first proximal piezo sensor 91 is bent during a radial deflection of the forward indicating radially deflectable proximal cantilever arm 9.1 and the second proximal piezo sensor 92 is bent during a radial deflection of the backward indicating radially deflectable proximal cantilever arm 9.2, each proximal piezo sensor 91, 92 emitting a signal to the chip 82 in response to being bent. The voltage output from any of the piezo sensors is sufficient to wake the processor in the chip 82.

Figure 3A:
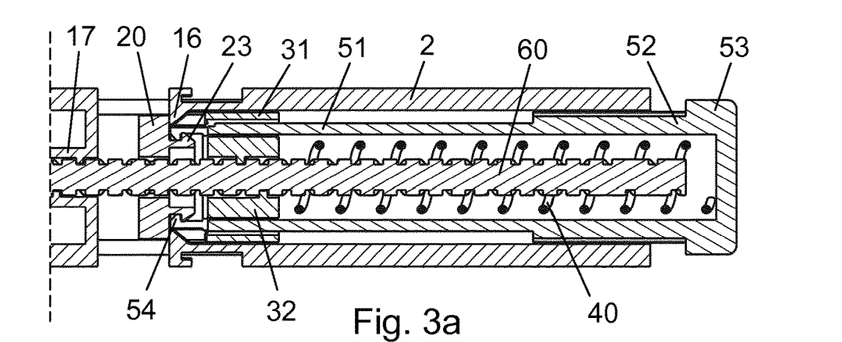
Figure 3B:
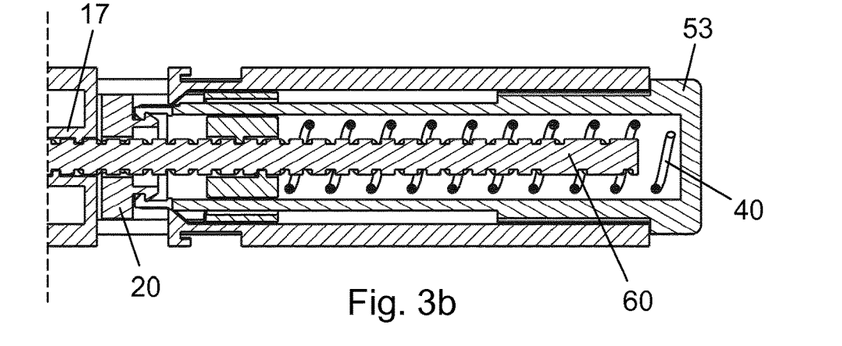

FIGS. 3a and 3b are both longitudinal section views of (approximately) the proximal half of the pen injection device 1, respectively just before setting of the first dose and just after completed expelling of the first dose.

Figure 4A:
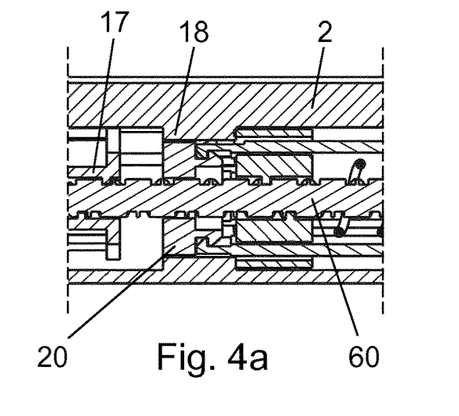
FIGS. 4a and 4b are longitudinal section views of a portion of the injection device in another sectional plane.
Figure 4B:
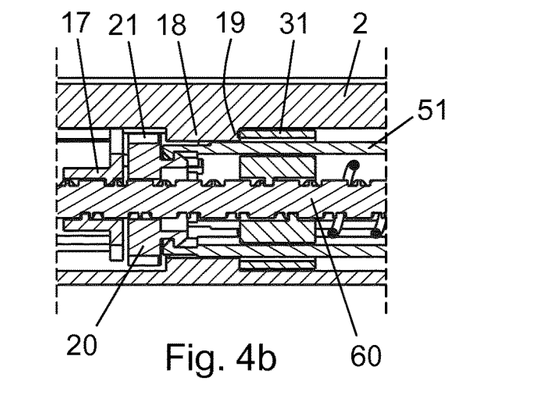

FIG. 4a is a longitudinal section view in another sectional plane of a central part of the pen injection device 1 in the state shown in FIG. 3a, and FIG. 4b is, similarly, a longitudinal section view in another sectional plane of a central part of the pen injection device 1 in the state shown in FIG. 3*b*.

Hence, FIGS. 3*a* and 4*a* show the interrelated positions of the various components in a dose setting state of the pen injection device 1. Specifically, it can be seen from FIG. 3*a* that in the dose setting state the end button 53 is axially spaced apart from the proximal end of the housing 2 by the compression spring 40, and that the interface between the hooked fingers 54 and the hooked stub 23 accordingly maintains the clutch 20 in the proximal dose setting position. In this position the clutch 20 is rotationally locked with respect to the housing 2 due to an engagement between the toothed rim 21 and a number of longitudinal splines 18 (see FIG. 4*a*) formed internally in the housing. The clutch 20 is prevented from further proximal displacement beyond this position by a stop surface 16 in the housing 2.

FIGS. 3*b* and 4*b*, on the other hand, show the interrelated positions of the various components in a drug expelling state of the pen injection device 1, more particularly at the end of a drug expelling action performed by the drug expelling mechanism, and while the end button 53 is depressed against the housing 2 (see FIG. 3*b*). It is noted that in such a depressed state of the dose dial knob 50 the hooked fingers 54 have forced the clutch 20 into the distal dose expelling position, where the toothed rim 21 is disengaged from the splines 18 (see FIG. 4*b*). It is also noted that at the end of a drug expelling action the outer annular wall 31 of the setting nut 30 rests against an end-of-dose stop 19 in the housing 2, constituted by respective proximal end surfaces of the splines 18 (see FIG. 4*b*).

Figure 5:
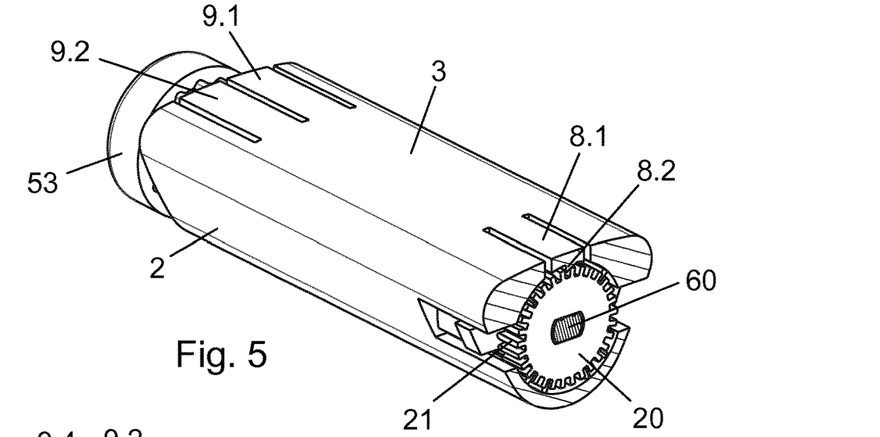
FIG. 5 is a perspective view of a proximal portion of the injection device housing, showing the dose delivery detection mechanism.

FIG. 5 is a perspective view cross-sectioned to illustrate the interaction between the clutch 20 and the central cantilever arm 8.1 during a drug expelling action. When the clutch 20 rotates in the dose expelling position the toothed rim 21 moves along an interior wall surface of the housing 2 and as a tooth on the toothed rim 21 passes an inwardly directed protrusion 8.2 on the central cantilever arm 8.1 the central cantilever arm 8.1 is deflected radially outwardly and back, producing a click. The angular displacement of the clutch 20 is correlated with the amount of drug expelled, due to the rotational interlocked relationship between the clutch 20 and the piston rod 60, and in this embodiment each such returned deflection of the central cantilever arm 8.1 corresponds to one incremental unit of drug having been expelled. A user of the pen injection device 1 may thus be able to determine the administered dose by counting the number of clicks from the central cantilever arm 8.1.

Figure 6:
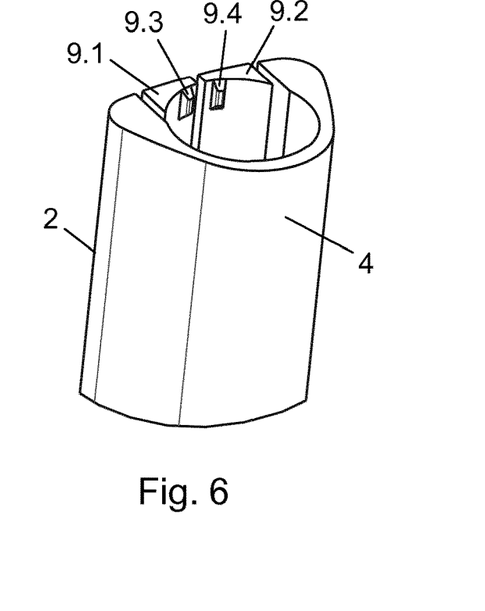
FIG. 6 is a proximal perspective view of a proximal portion of the injection device housing.

FIG. 6 is a perspective view of the proximal end portion of the housing 2 showing interior wall portions of the proximal cantilever arms 9.1, 9.2. It can be seen that the forward indicating radially deflectable proximal cantilever arm 9.1 is provided with an inwardly directed protrusion 9.3 and the backward indicating radially deflectable proximal cantilever arm 9.2 is provided with another inwardly directed protrusion 9.4.

Figure 7:
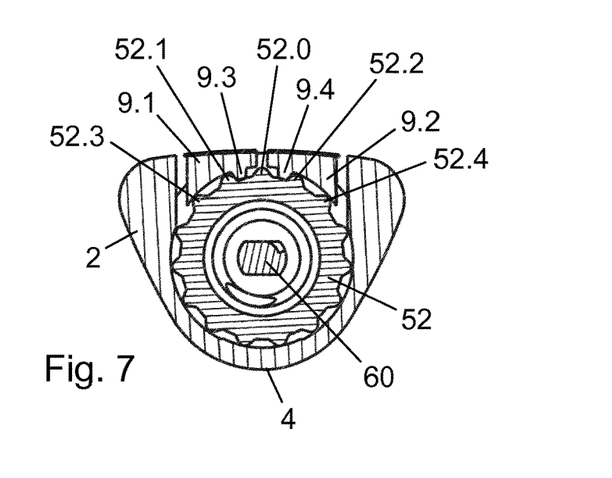
FIG. 7 is a cross-sectional view of the injection device, showing the dose setting detection mechanism.

FIG. 7 is a cross-sectional view of the pen injection device 1 through a proximal end portion, illustrating the interaction between the corrugated collar 52 and the proximal cantilever arms 9.1, 9.2 during a dose setting action. As the corrugated collar 52 forms part of the dose dial knob 50 a rotation of the end button 53 causes a corresponding rotation of the corrugated collar 52. In the relative positions of the corrugated collar 52 and the housing 2 shown in FIG. 7 a central ridge 52.0 is positioned between the inwardly directed protrusions 9.3, 9.4, while a first left ridge 52.1 immediately to the left of the central ridge 52.0 is positioned adjacent to a left flank of the inwardly directed protrusion 9.3 and a first right ridge 52.2 immediately to the right of the central ridge 52.0 is positioned adjacent to a right flank of the inwardly directed protrusion 9.4.

A clockwise rotation of the end button 53 from this position will cause firstly the first left ridge 52.1 to start passing the inwardly directed protrusion 9.3, thereby deflecting the forward indicating radially deflectable proximal cantilever arm 9.1, and immediately thereafter the central ridge 52.0 to start passing the inwardly directed protrusion 9.4, thereby deflecting the backward indicating radially deflectable proximal cantilever arm 9.2.

Conversely, a counter-clockwise rotation of the end button 53 from the shown position will cause firstly the first right ridge 52.2 to start passing the inwardly directed protrusion 9.4, thereby deflecting the backward indicating radially deflectable proximal cantilever arm 9.2, and immediately thereafter the central ridge 52.0 to start passing the inwardly directed protrusion 9.3, thereby deflecting the forward indicating radially deflectable proximal cantilever arm 9.1. Each time a ridge on the corrugated collar 52 passes one of the inwardly directed protrusions 9.3, 9.4 a click is produced.

The angular displacement of the dose dial knob 50 is correlated with the axial displacement of the setting nut 30, due to the engagement between the respective spacer legs 35 and slots 55 and a threaded connection between the nut structure 32 and the piston rod 60, and thereby determines the dose set for delivery. In this embodiment each unique pair of deflections of the proximal cantilever arms 9.1, 9.2 caused by two neighbouring ridges on the corrugated collar 52 passing a respective one of the inwardly directed protrusions 9.3, 9.4 in succession corresponds to a change of the set dose by one incremental unit.

In other words, if for example the end button 53 is rotated clockwise from the position shown in FIG. 7 a change of the dose by one unit occurs when the first left ridge 52.1 has passed the inwardly directed protrusion 9.3 and the central ridge 52.0 has subsequently passed the inwardly directed protrusion 9.4, the angular displacement of these two ridges having produced a first forward indicating unique pair of deflections of the proximal cantilever arms 9.1, 9.2. Further clockwise rotation of the end button 53 will cause another change of the dose by one unit to occur when a second left ridge 52.3 immediately to the left of the first left ridge 52.1 has passed the inwardly directed protrusion 9.3 and the first left ridge 52.1 has subsequently passed the inwardly directed protrusion 9.4, the angular displacement of these two ridges having produced a second forward indicating unique pair of deflections of the proximal cantilever arms 9.1, 9.2, and so forth.

On the other hand, if the end button 53 is rotated counter-clockwise from the position shown in FIG. 7 a change of the dose by one unit occurs when the first right ridge 52.2 has passed the inwardly directed protrusion 9.4 and the central ridge 52.0 has subsequently passed the inwardly directed protrusion 9.3, the angular displacement of these two ridges having produced a first backward indicating unique pair of deflections of the proximal cantilever arms 9.1, 9.2. Further counter-clockwise rotation of the end button 53 will cause another change of the dose by one unit to occur when a second right ridge 52.4 immediately to the right of the first right ridge 52.2 has passed the inwardly directed protrusion 9.4 and the first right ridge 52.2 has subsequently passed the inwardly directed protrusion 9.3, the angular displacement of these two ridges having produced a second backward indicating unique pair of deflections of the proximal cantilever arms 9.1, 9.2, and so forth.

Specifically, each forward indicating unique pair of deflections causes an incremental increase of the set dose by one unit and each backward indicating unique pair of deflections causes an incremental decrease of the set dose by one unit.

In the following the invention will be described in connection with a use of the pen injection device 1 according to the first embodiment.

In FIG. 2 the pen injection device 1 is in the dose setting state, where the end button 53 is axially spaced apart from the housing 2. In this state a dose to be delivered from the cartridge 10 is set by the user rotating the end button 53 about the longitudinal axis.

The piston rod 60 comprises a first non-self-locking thread, which mates with a thread in the nut member 17 and an overlapping oppositely handed second non-self-locking thread which mates with a thread in the nut structure 32, providing a mechanical advantage of 2:1.

Due to the rotationally interlocked relationship between the setting nut 30 and the dose dial knob 50 the nut structure 32 will travel proximally along the second non-self-locking thread of the piston rod 60 when the end button 53 is rotated clockwise (seen from the proximal end of the pen injection device 1) in a dial up action, the clutch 20 in its dose setting position preventing the piston rod 60 from rotation relative to the housing 2. The proximal displacement of the setting nut 30 will compress the compression spring 40 which thereby stores energy.

The dose dial knob 50 is prevented from rotating in the absence of a user induced torque to the end button 53 due to the engagement between the corrugated collar 52 and the respective inwardly directed protrusions 9.3, 9.4, even when the compression spring 40 experiences a maximum in-use compression. An unintended distal return displacement of the setting nut 30 caused by a prematurely expanding compression spring 40 is thereby prevented. Hence, as long as the clutch 20 is in its dose setting position, where the piston rod 60 is prevented from rotating, the setting nut 30 cannot perform a translational motion with respect to the housing 2 and can only perform a helical distal motion along the second non-self-locking thread, if the user rotates the end button 53 counter-clockwise in a dial down action. The compression spring 40 thus remains compressed when the user has completed the dose setting action.

In accordance with the setting nut 30 moving along the second non-self-locking thread of the piston rod 60 the ridges on the corrugated collar 52 passes the respective inwardly directed protrusions 9.3, 9.4, causing deflections of the forward indicating radially deflectable proximal cantilever arm 9.1 and the backward indicating radially deflectable proximal cantilever arm 9.2, as described above. At each deflection of the forward indicating radially deflectable proximal cantilever arm 9.1 the first proximal piezo sensor 91 emits a first sensor signal and at each deflection of the backward indicating radially deflectable proximal cantilever arm 9.2 the second proximal piezo sensor 92 emits a second sensor signal.

Each forward indicating unique pair of deflections in accordance with the above described thus prompts a forward indicating unique signal pair, $SP_f$, consisting of a first sensor signal followed by a second sensor signal. The chip 82 is configured to update the display 81 by an incremental increase in the form of a unit being added to the currently displayed number immediately upon registration of such a forward indicating unique signal pair.

Correspondingly, each backward indicating unique pair of deflections in accordance with the above described prompts a backward indicating unique signal pair, $SP_b$, consisting of a second sensor signal followed by a first sensor signal, and the chip 82 is configured to update the display 81 by an incremental decrease in the form of a unit being subtracted from the currently displayed number immediately upon registration of such a backward indicating unique signal pair. The display 81 accordingly provides a real-time electronic visual indication of the set dose.

Figure 8:
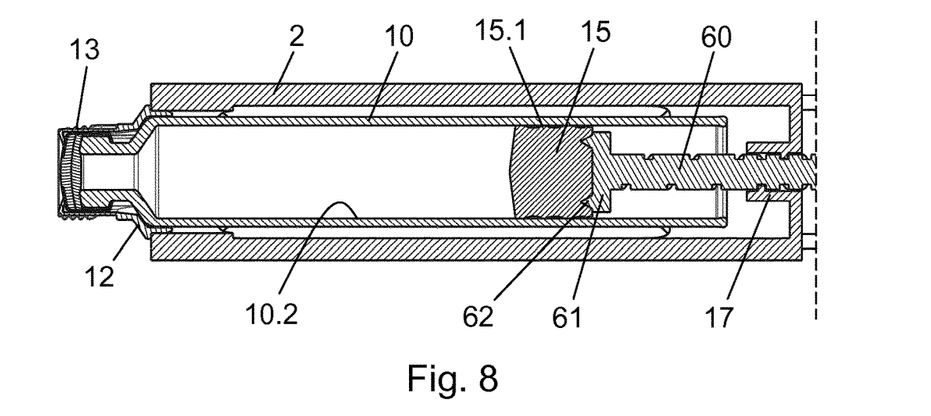
FIG. 8 is a longitudinal section view of a portion of the injection device showing an exemplary coupling between the piston and the piston rod member.

A depression of the end button 53 against the housing 2 to expel a set dose (ref. FIG. 3b) causes the hooked fingers 54 to urge the clutch 20 distally into its dose expelling position, thereby disengaging the toothed rim 21 from the splines 18 (ref. FIG. 4b) and releasing the compression spring 40. The stored energy therefrom pushes the setting nut 30 distally, and the resulting translational motion of the nut structure 32 causes the piston rod 60 and the clutch 20 to rotate. The piston rod 60 is thus advanced helically through the nut member 17 and the spikes 62 on the piston rod foot 61 cause the piston 15 to undergo a helical distal movement relative to the cartridge 10, thereby expelling the set dose of drug through an attached injection needle (not shown). FIG. 8 is a longitudinal section view of (approximately) the distal half of the pen injection device 1, showing the rotational interlocking connection between the piston rod 60 and the piston 15.

The initial helical movement of the piston 15, as opposed to a conventional initial compression thereof, introduces a friction in the contact interface between the piston 15 and the cartridge 10 which increases the resistance to the rotation of the piston rod 60 notably. The friction, which occurs between a peripheral portion 15.1 of the piston 15 and an interior surface 10.2 of the cartridge body 10.1, is a velocity dependent viscous friction which in embodiments of the invention where the drug expelling mechanism is powered by a spring becomes particularly pronounced since the initial spring force (or torque) is high in order to account for the inherent decline in produced force (or torque) as the spring gradually relaxes.

Consequently, the rotation of the clutch 20 is slowed down and the time between the clicks produced by the central cantilever arm 8.1 is increased sufficiently to enable a clear distinction between two successive clicks, both electronically and by the human ear.

The drug expelling continues until the outer annular wall 31 abuts the end-of-dose stop 19 at which point the piston rod 60, and thereby also the clutch 20, stops rotating. In accordance with the angular displacement of the clutch 20 during the drug expelling action the teeth of the toothed rim 21 pass the inwardly directed protrusion 8.2, causing deflections of the central cantilever arm 8.1, as described above. At each deflection of the central cantilever arm 8.1 the central piezo sensor emits a central sensor signal, $S_c$, and the chip 82 is configured to update the display 81 by an incremental decrease in the form of a unit being subtracted from the currently displayed number immediately upon registration of such a central sensor signal. The display 81 accordingly also provides a real-time electronic visual indication of the dose of drug being expelled.

During a normally progressing dose delivery the display 81 will show a dose count-down until the outer annular wall 31 reaches the end-of-dose stop 19 and the clutch 20 stops rotating, at which point a '0' or some other indication of a completed drug expelling action will be displayed. However, the chip 82 is further configured to update the display 81 to display an error indication, such as e.g. '- -', in case the number of received central sensor signals does not equal the number of registered forward indicating unique signal pairs minus the number of backward indicating unique signal pairs, i.e. in case $\Sigma S_c \neq \Sigma SP_f - \Sigma SP_b$.

For every normally progressing dose delivery (where $\Sigma S_c = \Sigma SP_f - \Sigma SP_b$) the chip 82 is configured to store a value representing the size of the dose delivered and a corresponding time of delivery. The stored data may be forwarded to, or requested by, an exterior device (not shown) via e.g. a wireless communication link (not shown).

Figure 9:
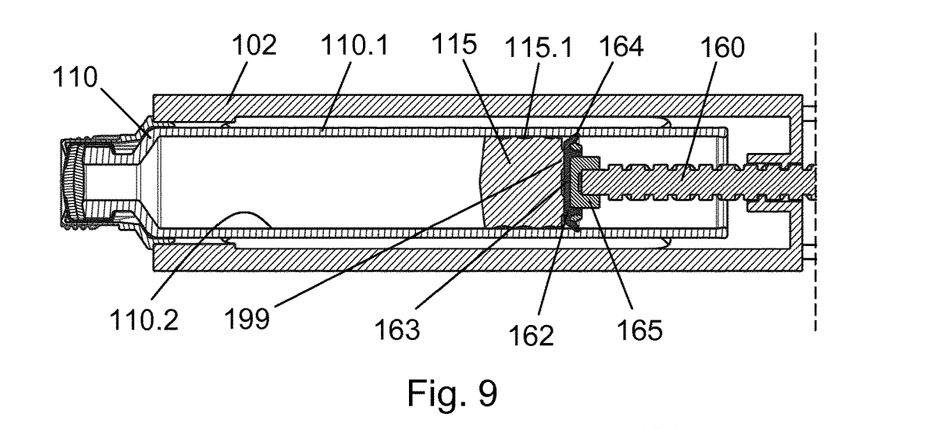
FIG. 9 is a longitudinal section view of a portion of an injection device according to another exemplary embodiment of the invention.

FIG. 9 is a longitudinal section view of a distal portion of a pen injection device according to another embodiment of the invention. Specifically, the figure shows a cartridge 110 with a cartridge body 110.1 accommodated in a housing 102. A piston rod 160 is configured to exert a pressure on and apply a torque to a piston 115 of the cartridge 110 via a two-component piston washer 161 (see FIG. 10) in order to expel a dose of drug contained in the cartridge 110. The pen injection device according to this second embodiment of the invention is principally and functionally similar to the previously disclosed pen injection device 1, only the rotational coupling between the piston 115 and the piston rod 160 differing from the previous solution.

The piston washer 161 comprises a rigid washer core 165 and a softer interface body 162, the latter providing both a distal end face 163 suited for interaction with the piston 115 and a lip 164 for mechanical connection with an interior surface 110.2 of the cartridge body 110.1. More specifically, the distal end face 163 is adapted to abut a proximal end face of the piston 115 which has a plurality of protrusions 199. The washer core 165 and the interface body 162 are fixedly connected, i.e. no relative rotational motion between the two can occur.

Figures 10, 11:
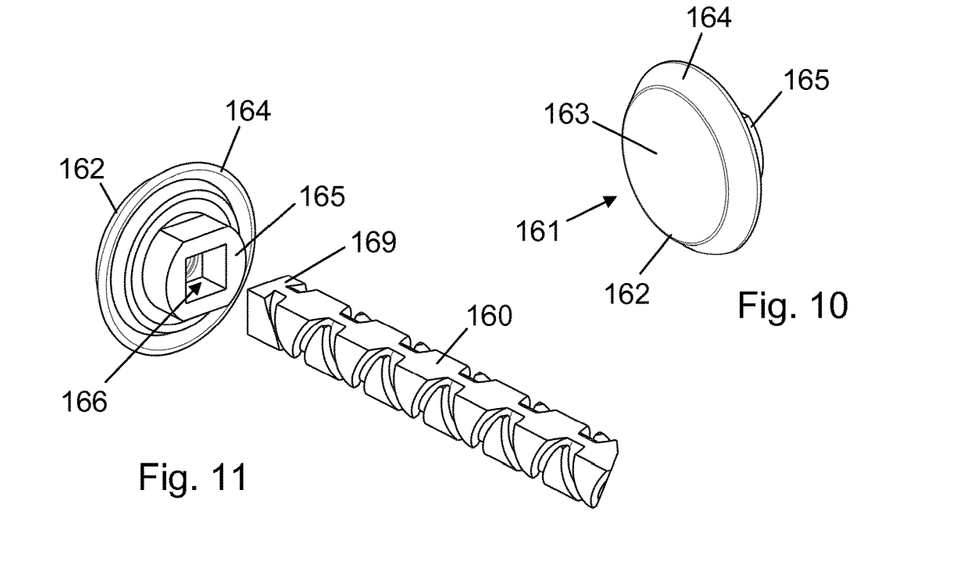
FIG. 10 is a perspective front view of the piston washer employed in the injection device of FIG. 9.
FIG. 11 is a perspective rear view of the piston washer with the appurtenant piston rod.

FIG. 10 is a perspective distal view of the piston washer 161, while FIG. 11 is a perspective proximal view of the piston washer 161 also showing a distal portion of the piston rod 160. As can be seen the piston rod 160 has a non-circular cross-section and a square distal end 169. The washer core 165 is shaped to provide a proximally facing cavity 166 which is configured to receive the square distal end 169, thereby providing a rotationally interlocked connection between the piston rod 160 and the piston washer 161. Hence, each angular displacement of the piston rod 160 relative to the housing 102 is transferred to the piston washer 161.

The lip 164 interfacing with the interior surface 110.2 of the cartridge body 110.1 provides a frictional resistance to angular displacement of the piston washer 161 which in itself is sufficient to decrease the initial speed of rotation of the piston rod 160 to a level that enables an audible and/or electronic distinction of the first clicks.

Furthermore, however, in this particular embodiment the interface body 162 is made of a material which is softer than the proximal end face of the piston 115 and which has a higher compression set than the piston 115. This results in the protrusions 199 sinking into the distal end face 163 when the piston washer 161 and the piston 115 are pressed against one another, the protrusions practically avoiding deformation themselves. The interface body 162 is a TPE having a compression set of about 60%. After only a few hours of pressurised contact the adherence of the distal end face 163 to the proximal end face of the piston 115 is so strong that a rotationally interlocked connection between the piston washer 161 and the piston 115 has been established, and a rotation of the piston rod 160 will thus result in a slaved rotation of the piston 115, whereby a peripheral portion 115.1 of the piston 115 will slide along the interior surface 110.2 of the cartridge body 110.1, providing an additional contribution to the braking of the piston rod 160.

Figure 12:
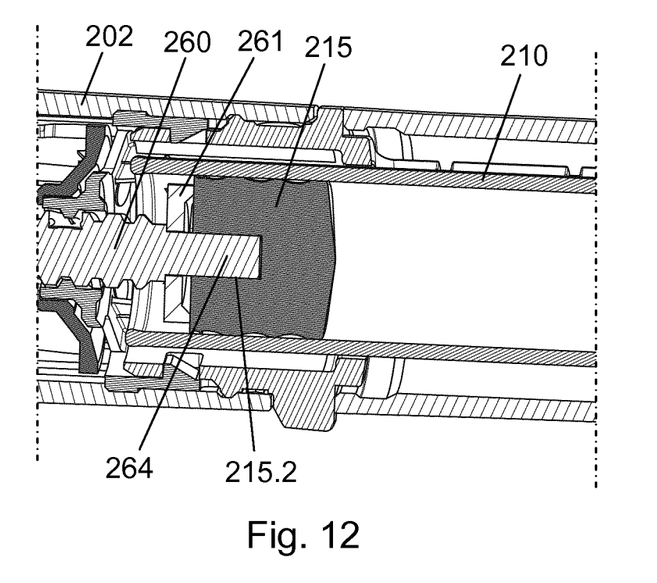
FIG. 12 is a longitudinal section view of a portion of an injection device according to a further exemplary embodiment of the invention.

FIG. 12 is a longitudinal section view of a central portion of an injection device according to yet another exemplary embodiment of the invention. The figure shows a cartridge 210 attached to a housing 202 and sealed by a piston 215. A piston rod 260 is threadedly engaged with the housing 202 and adapted to advance helically in the distal direction during dose administration. A piston rod foot 261 is arranged about a distal portion of the piston rod 260 in a manner whereby axial displacement of the piston rod 260 is transferred to the piston rod foot 261 and further transferred to the piston 215.

The piston rod 260 ends in a distal stud 264 which is accommodated tightly in a recess 215.2 in the proximal portion of the piston 215. When the piston rod 260 rotates the stud 264 undergoes a friction influenced motion relative to the recess 215.2, due to the non-rotating piston 215, which slows down the piston rod 260. The angular displacement of the piston rod 260 is thus easier to determine, e.g. using a mechanism similar to the above described.

Figure 13:
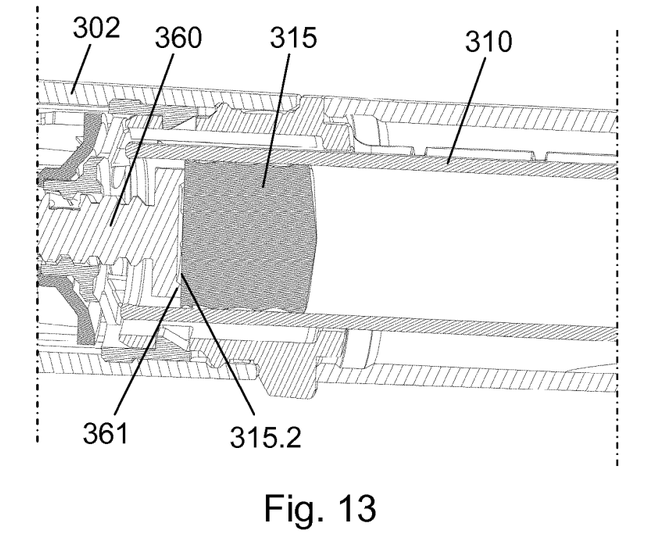
FIG. 13 is a longitudinal section view of a portion of an injection device according to an even further exemplary embodiment of the invention.

FIG. 13 is a longitudinal section view of a central portion of an injection device according to yet another exemplary embodiment of the invention. The figure shows a cartridge 310 attached to a housing 302 and sealed by a piston 315. A piston rod 360 is threadedly engaged with the housing 302 and adapted to advance helically in the distal direction during dose administration.

A piston rod foot 361 is formed integrally with the piston rod 360 at the distal end of thereof. The piston rod foot 361 is arranged in abutment with a proximal end surface 315.2 of the piston 315 and accordingly undergoes a friction influenced motion relative to the proximal end surface 315.2, due to the non-rotating piston 315, during rotation of the piston rod 360, i.e. during dose administration. The rotation of the piston rod 360 is thus slowed down, enabling capture of every signal produced by e.g. a cantilever arm similar to the one described above.

The invention claimed is:

1. A pen-type injection device comprising:
a housing extending along a general axis,
a cartridge comprising a cartridge body, a penetrable septum, and a piston, together defining a variable volume reservoir adapted to hold a liquid substance, the cartridge being rotationally fixed with respect to the housing,
a dose expelling mechanism for expelling a dose of the liquid substance from the cartridge, comprising a piston rod structure for advancing the piston, the piston rod structure comprising:
a piston rod threadedly engaged with the housing and adapted to rotate and thereby undergo helical motion relative to the cartridge body during dose expelling, and
a piston rod foot rotationally locked to the piston rod and adapted to interface with the piston, and
output structure producing a detectable output at an angular displacement of the piston rod which corresponds to expelling of a predetermined dose increment, a total number of detectable outputs produced during a dose expelling event thereby being indicative of a size of an expelled dose,
wherein the pen-type injection device further comprises a brake mechanism configured to slow down rotational motion of the piston rod, the brake mechanism comprising a first contact surface forming part of the cartridge body, and a second contact surface arranged, or adapted to be arranged, in contact with the first contact surface and being rotationally locked with respect to the piston rod structure.

2. The pen-type injection device according to claim 1, wherein the detectable output is a tactile and/or audible output.

3. The pen-type injection device according to claim 1, further comprising a detection mechanism configured to electronically register the detectable output.

4. The pen-type injection device according to claim 3, wherein the output structure comprises a deflectable housing portion capable of deflection relative to other housing portions and an activation element rotationally locked with respect to the piston rod structure and arranged to deflect the deflectable housing portion in response to undergoing the specific angular displacement relative to the housing, and
wherein the detection mechanism comprises a sensor arranged on the deflectable housing portion and adapted to detect a deflection thereof, and a processor electronically connected with the sensor and configured to process deflections detected by the sensor.

5. The pen-type injection device according to claim 1, wherein the second contact surface forms part of the piston, and the piston and the piston rod are rotationally interlocked.

6. The pen-type injection device according to claim 5, wherein the piston rod foot comprises a plurality of spaced protrusions which are pressed into respective peripheral portions of the piston.

7. The pen-type injection device according to claim 1, wherein the second contact surface forms part of the piston rod foot.

8. The pen-type injection device according to claim 7, wherein the piston comprises a first interface material having a first hardness and a first compression set, and the piston rod foot comprises a second interface material having a second hardness which is smaller than the first hardness and a second compression set which is higher than the first compression set, the second interface material being arranged in pressurised abutment with the first interface material.

9. The pen-type injection device according to claim 8, wherein the second contact surface is formed from the second interface material.

10. The pen-type injection device according to claim 1, further comprising an energy storage unit for providing energy to effect a rotation of the piston rod.

* * * * *